United States Patent
Soergel et al.

(10) Patent No.: US 9,261,466 B2
(45) Date of Patent: Feb. 16, 2016

(54) DEVICE FOR DETERMINING A COMPOSITION OF A FUEL MIXTURE BY MEANS OF A COAXIAL WAVEGUIDE THROUGH WHICH THE FUEL MIXTURE IS FLOWING

(75) Inventors: Werner Soergel, Pforzheim (DE); Dirk Schmidt, Kirchheim (DE)

(73) Assignee: ROBERT BOSCH GMBH, Stuttgart (DE)

(*) Notice: Subject to any disclaimer, the term of this patent is extended or adjusted under 35 U.S.C. 154(b) by 527 days.

(21) Appl. No.: 13/698,613

(22) PCT Filed: Mar. 22, 2011

(86) PCT No.: PCT/EP2011/054318
§ 371 (c)(1),
(2), (4) Date: Jan. 25, 2013

(87) PCT Pub. No.: WO2011/144377
PCT Pub. Date: Nov. 24, 2011

(65) Prior Publication Data
US 2013/0111980 A1    May 9, 2013

(30) Foreign Application Priority Data
May 17, 2010    (DE) .......................... 10 2010 029 007

(51) Int. Cl.
*G01N 30/95* (2006.01)
*G01N 30/62* (2006.01)
(Continued)

(52) U.S. Cl.
CPC .............. *G01N 22/00* (2013.01); *F02D 19/087* (2013.01); *F02M 25/0227* (2013.01);
(Continued)

(58) Field of Classification Search
CPC ................... G01N 33/2852; G01N 33/332847
USPC ......................................... 73/61.61
See application file for complete search history.

(56) References Cited

U.S. PATENT DOCUMENTS

| | | | |
|---|---|---|---|
| 3,812,422 | A | 5/1974 | De Carolis |
| 4,345,202 | A | 8/1982 | Nagy et al. |

(Continued)

FOREIGN PATENT DOCUMENTS

| | | |
|---|---|---|
| BR | 0 204 519 | 6/2004 |
| DE | 34 12 704 | 10/1984 |

(Continued)

OTHER PUBLICATIONS

Santos E J P : "Determination of ethanol content in gasoline : theory and experiment", Microwave and Optoelectronics Conference, 2003. IMOC 2003. Proceedings of the 2003 SBMO/IEEE MTT-S International Sep. 20-23, 2003, Piscataway, NJ, USA, IEEE, US, vol. 1, Sep. 20, 2003, pp. 349-353, XP010669611, DOI : 10.1109/IMOC.2003. 1244884, ISBN : 978-0-7803-7824-7.

(Continued)

*Primary Examiner* — Hezron E Williams
*Assistant Examiner* — Rodney T Frank
(74) *Attorney, Agent, or Firm* — Kenyon & Kenyon LLP

(57) ABSTRACT

A device for determining a composition of a fuel mixture is provided, in particular for determining an ethanol component and/or a water component in the fuel mixture. The device includes at least one housing having at least one electrically conductive housing element through which the fuel mixture is able to flow. At least one internal conductor, which is at least partially enclosed by the housing element, is introduced into the housing element. In addition, the device has at least one connection device for the coupling of microwave signals.

15 Claims, 2 Drawing Sheets

(51) Int. Cl.
*G01N 22/00* (2006.01)
*G01N 33/28* (2006.01)
*F02M 25/022* (2006.01)
*F02D 19/08* (2006.01)

(52) U.S. Cl.
CPC ...... *F02M 25/0228* (2013.01); *G01N 33/2852* (2013.01); *F02D 19/084* (2013.01); *Y02T 10/121* (2013.01); *Y02T 10/36* (2013.01)

(56) References Cited

U.S. PATENT DOCUMENTS

| | | | |
|---|---|---|---|
| 4,503,384 | A | 3/1985 | Nagy et al. |
| 4,580,441 | A | 4/1986 | Sakurai et al. |
| 4,862,060 | A | 8/1989 | Scott et al. |
| 5,361,035 | A | 11/1994 | Meitzler et al. |
| 6,121,780 | A | 9/2000 | Cruickshank et al. |
| 2004/0123851 | A1* | 7/2004 | Schmidt et al. ............... 123/606 |
| 2004/0135585 | A1 | 7/2004 | Nagy |
| 2004/0234916 | A1* | 11/2004 | Hale et al. ..................... 431/358 |
| 2005/0253599 | A1 | 11/2005 | Vanzullen et al. |
| 2005/0258159 | A1* | 11/2005 | Hale et al. ..................... 219/270 |
| 2010/0196208 | A1* | 8/2010 | Makita et al. ................... 422/83 |

FOREIGN PATENT DOCUMENTS

| | | |
|---|---|---|
| DE | 10 2006 034884 | 4/2007 |
| DE | 10 2008 044 383 | 6/2010 |
| GB | 1 314 368 | 4/1973 |
| SU | 759 927 | 8/1980 |
| WO | 2005/109012 | 11/2005 |

OTHER PUBLICATIONS

Weiss M et al : "A Novel Method of Determining the Permittivity of Liquids", IEEE Transactions on Instrumentation and Measurement, IEEE Service Center, Piscataway, NJ, US, vol. 49, No. 3, Jun. 1, 2000, pp. 488-492, XP000937372, ISSN : 0018-9456, DOI : 10.1109/19.850381.

Kent M et al : "Design Note ; A simple flowthrough cell for microwave dielectric measurements", Journal of Physics E. Scientific Instruments, IOP Publishing, Bristol, GB, vol. 22, No. 4, Apr. 1, 1989, pp. 269-271, XP020018983, ISSN : 0022-3735, DOI : 10.1088/0022-3735/22/4/012.

Henrik H Nissen et al: "Time Domain Reflectometry Developments in Soil Science: II. Coaxial Flow Cell for Measuring Effluent Electrical Conductivity", Soil Science, vol. 168, No. 2, Feb. 1, 2003, pp. 84-89, XP55006073, DOI: 10.1097/01.ss.0000055303.23789.39 abstract; figure 1.

Kurt C Lawrence et al: "Flow-Through Coaxial Sample Holder Design for Dielectric Properties Measurements from 1 to 350 MHz", IEEE Transactions on Instrumentation and Measurement, IEEE Service Center, Piscataway, NJ, US, vol. 47, No. 2, Apr. 1, 1998, XP0110244841, ISSN: 0018-9456, p. 365, figures 1,6,7.

Hudiara I S et al: "Microwave properties of commercial petrol over 900 MHz to 9 GHz",.Journal of the Institution of Electronics and Telecommunication Engineers, Engineers, New Dehli, vol. 40, No. 5-6, Sep. 1, 1994, pp. 291-292, XP009151679, ISSN : 0377-2063.

\* cited by examiner

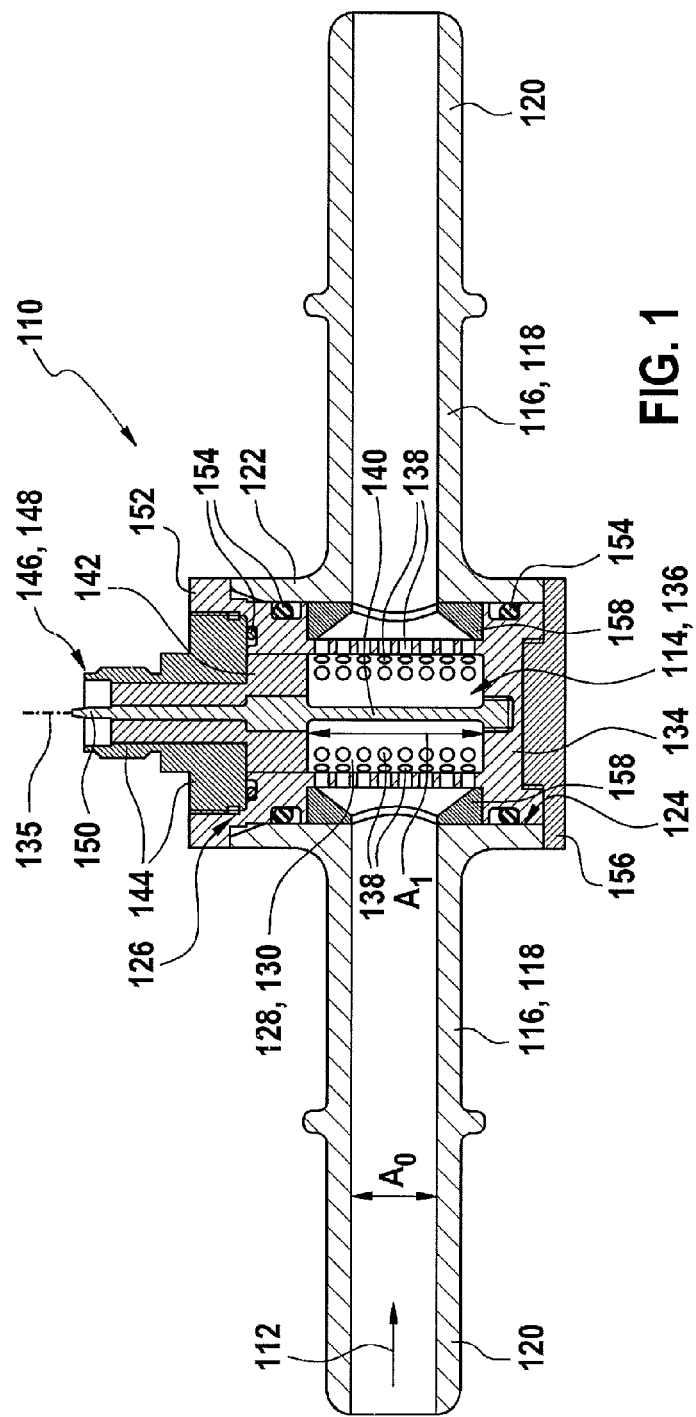
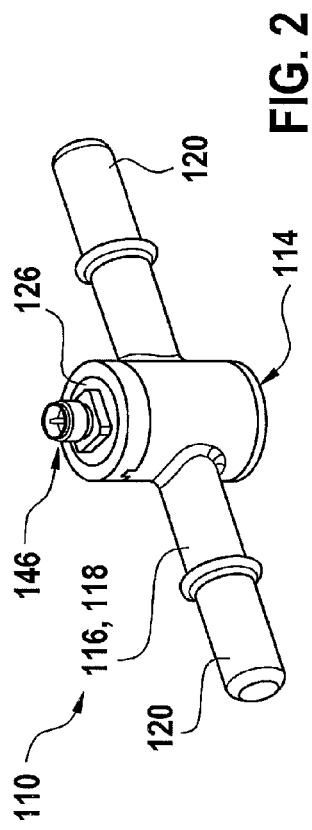
FIG. 1
FIG. 2

DEVICE FOR DETERMINING A COMPOSITION OF A FUEL MIXTURE BY MEANS OF A COAXIAL WAVEGUIDE THROUGH WHICH THE FUEL MIXTURE IS FLOWING

FIELD OF THE INVENTION

The present invention relates to a device for determining a composition of a fuel mixture by a coaxial waveguide through which the fuel mixture is flowing.

BACKGROUND INFORMATION

Methods and devices for determining the composition of fuel mixtures are believed to be understood from the related art. For example, the use of fuel mixtures which, in addition to the actual mineral oil fuels, are able to process an admixture of ethanol and/or other alcohols is increasing in the motor vehicle sector. As a rule, the parameters of the engine control of the motor vehicle are adapted to the composition of the fuel mixture. However, in some cases this may require knowledge of the composition of the fuel mixture, especially an ethanol/fuel mixture ratio. One measuring method consists of measuring an absorption, transmission or reflection of microwaves through the fuel mixture. An example of a device set up for this purpose is discussed in DE 34 12 704 A1.

Moreover, a method for determining a composition of a fuel mixture is discussed in post-published DE 10 2008 044 383.2. Here, a characteristic behavior of a particular response to incident microwave radiation is recorded across a greater frequency range in order to determine the characteristics of the fuel mixture, and the composition of the fuel mixture is inferred therefrom. One particular advantage of the method discussed in DE 10 2008 044 383.2 is that it can increase the precision by using greater frequency ranges, so that, for example, alcohol-fuel mixtures that additionally also contain a water component and/or additives, are able to be characterized much more accurately than when using conventional methods. However, there is potential for improvement with regard to the incoupling and outcoupling of the microwave signals into or out of the fuel.

SUMMARY OF THE INVENTION

Accordingly, a device and a method are provided, which are able to be used to determine a composition of a fuel mixture. This makes it possible, in particular, to utilize dielectric characteristics of fuels for determining the ethanol content of fuel mixtures. As an alternative or in addition, other components of the fuel mixture, e.g., water components or components of additives, are able to be determined in quantitative terms. The device in particular may be developed as a measuring sensor, i.e., a device which, for instance, may be integrated into a fuel line and/or some other type of flow pipe or a fluid storage device and provides measuring results without having any significant effect on the characteristic of the fluid flow.

The device includes at least one housing. For instance, as discussed in greater detail below, this housing may have at least one flow pipe section. The housing may consist of several parts, in particular. The provided housing includes at least one electrically conductive, e.g., metallic, housing element, through which the fuel mixture is able to flow. As will be described in greater detail further below, this housing element may be a sleeve or a cup, in particular. Specifically, this housing element may have a cylindrical design and be introduced into the housing perpendicularly to a flow direction of the fuel. However, other designs are possible as well. The housing element may be produced from a fuel-resistant material, such as a fuel-resistant metal, e.g., stainless steel or some other metallic material. One material in particular is type 1.4301 stainless steel.

At least one internal conductor is inserted into the housing element. An internal conductor is a metallic conductor which is able to conduct electrical signals. The internal conductor may be developed in the form of a wire and/or pin, for example, and may have an essentially straight form. During the flow through the housing element the internal conductor may be in contact with the fuel mixture. The internal conductor is at least partially enclosed by the housing element. For instance, this may be accomplished in that the internal conductor is coaxially enclosed by the housing element, so that it is accommodated inside the preferably cylindrical housing element, such as the cup, for instance in concentric manner. This means that the axis of the internal conductor and the axis of the housing element, e.g., the cup, which may coincide in principle, but slight deviations are allowed as well, for instance deviations of no more than 1 to 2 mm and no more than 5°. In addition the device has at least one connection device such as an electrical plug, to couple microwave signals into the device, especially into the internal conductor.

Coupling of microwave signals denotes an incoupling of microwave signals into the device, especially into the internal conductor and/or into the housing or housing components, and/or a decoupling of microwave signals from the device, especially from the internal conductor and/or the housing or housing parts. Microwave signals in general are electromagnetic high-frequency signals, which may lie in a frequency range of above 100 MHz or even 300 MHz, e.g., in a frequency range between 300 MHz and 300 GHz, especially between 300 MHz and 20 GHz, which may be between 500 MHz and 10 GHz, and especially, in a range of 0.5 and 8.5 GHz.

As explained above, the housing element may enclose the internal conductor, especially in coaxial manner. This means that, as explained above, at least sections of the internal conductor essentially run along an axis of the housing element in the interior of the housing element. For example, the housing element may be developed in the form of a cup, such as a metallic cup, which has a round and/or polygonal cross-section, for instance. The axis of the cup may extend through the device transversely to a flow direction of the fuel mixture, for instance transversely to a flow pipe axis. It is possible, for instance, that the cup axis in principle runs perpendicularly, i.e., for instance at an angle of 90°±20°, which may be 90°±10°, and especially, 90°±5°, in relation to a flow pipe axis. The cup in particular may have a closed cup bottom (which may be outside the flow cross-section). As a result, the cup could be described as a hollow cylinder which is sealed at one end by the cup bottom. The cup may be connected to the internal conductor in electrically conductive manner, especially in the region of the cup bottom. For instance, the internal conductor may project into the cup bottom, may be inserted into it (e.g., if the internal conductor is implemented as a plug pin) or be connected to the cup bottom in electrically conductive manner in some other way.

It is possible that the housing element, especially the cup, is provided with a plurality of bores through which the fuel may flow into and out of the interior of the cup. That is to say, the cup may have a plurality of bores. The bores may have a diameter that is considerably smaller than the lowest wavelength of the incoupled microwaves in the fuel mixture.

This avoids an outcoupling of microwaves forming between the internal conductor and the cup or the inner wall of the cup. The bores may have a diameter of less than 2 mm, especially less than 1 mm. For E100, for instance, i.e., fuel having a nominal ethanol component of 100%, the minimum wavelength $\lambda=7$ mm at a frequency f=19 GHz. The bores may basically have various cross-sections. Especially preferred may be round cross-sections, but even cross-sections that are not round are conceivable in principle. A "diameter" in the case of non-round cross-sections such as polygonal cross-sections is an "equivalent diameter", such as a diameter of a circle having the same opening area.

The connection device is to be used for the incoupling and/or outcoupling of microwave signals. In particular, this connection device may include a plug and/or a plug-in connection. Especially preferred in such a case may be standardized plug-in connections. For example, it is possible to use coaxial plugs in which at least one contact is provided for applying microwave signals to the internal conductor, that is to say, for the incoupling and/or outcoupling of microwave signals. If a coaxial plug is involved, the contact is enclosed by at least one shielding plug component. It is possible, for instance, to use SMA-RP plug connectors for this purpose.

As explained earlier, the device, especially the housing of the device, may include at least one flow pipe section through which the fuel mixture is able to flow in a particular flow direction. The internal conductor and the housing element may be introduced into the flow pipe section especially in transverse manner, which may be essentially perpendicularly (i.e., with the afore-described deviation tolerances) with respect to the direction of flow. For instance, the device may include a plug-in cartridge. The plug-in cartridge may include the internal conductor and the housing element and possibly additional elements. It is possible, for example, that the afore-described cup and the internal conductor introduced into the cup are accommodated in the plug-in cartridge. In a measuring region of the device, the plug-in cartridge is able to be plugged into a receptacle of the flow pipe section, transversely to the direction of flow.

The bores of the cup may then be aligned in such a way that they point in the flow direction, so that the fuel mixture is able to flow through the cup of the cartridge without any flow detour. The receptacle, for instance, may include a widened region in the housing, which has at least one receiving bore into which the cartridge is able to be plugged, transversely to the direction of flow. The plug-in receptacle is able to be implemented in reversible or also permanent form. Once the cartridge has been plugged in, it is able to be fixed in place in the receptacle, for instance using a screw-fitting or crimping connection, clamping rings or other types of fixation. Moreover, the plug-in cartridge may be sealed from the flow pipe section, especially by means of at least one sealing element. One, two, four or more O-rings, for example, may be provided for this purpose.

The afore-described connection device, for instance, may be situated on an end face of the cartridge, outside the flow pipe section, so that, for example, the flow pipe section, the cartridge and the connection device, e.g., the plug-in connection, form a T-configuration. Moreover, the flow pipe section may have two or more ports, such as an intake port and an outlet port. These ports could be standardized ports, e.g., in the form of cost-effective, standardized hydraulic ports, e.g., according to the SAE standard.

If the device has a flow pipe section through which the fuel mixture is able to flow, such as an essentially linear or straight flow pipe section provided with two hydraulic ports, for example, but also if other developments are involved, the internal conductor may be accommodated in a measuring region of the device, in particular. For instance, it is possible that the flow pipe section includes a flow pipe cross-section and the housing element and the internal conductor are accommodated in the measuring region. In the measuring region, the flow pipe cross-section may be widened in relation to the flow pipe cross-section outside the measuring region.

This means that the flow in the measuring region has a greater cross-section than in other regions of the device, e.g., regions of the flow pipe outside the measuring region. In other words, the flow in the measuring region may be broader. The broadening in particular may be achieved by providing one, two or more bushings in the measuring region, e.g., as part of the cartridge, which provide the widened area in the measuring region, for example, a continuous broadening, i.e., a broadened area having an essentially linear characteristic.

The bushings providing the broadening are able to prevent dead volumes at the transition between the flow pipe section and the measuring region, e.g., at the transition between the flow pipe section and the plug-in cartridge. The bushings may have an annular design, for example, and likewise be accommodated about the internal conductor in the plug-in cartridge in concentric manner. The bushings, for instance, may be manufactured from a plastic material such as a fuel-resistant plastic material, e.g., a fluorinated polyethylene.

According to one further aspect of the exemplary embodiments and/or exemplary methods of the present invention, a method for determining a composition of a fuel mixture is provided, in which a device as recited in one or more of the afore-described developments is used to couple microwave signals into the fuel mixture across a frequency range. The device is employed to receive response signals. Response signals, for example, may be reflected and/or transmitted signals which may likewise be outcoupled via the connection device, for instance. By comparing the incoupled microwave signals and the response signals, at least one parameter is determined as a function of the microwave frequency of the incoupled microwave signals. A characteristic of the parameter across the microwave frequency is used to infer the composition of the fuel mixture.

In so doing, it is basically possible to use the method of DE 10 2008 044 383.2. However, other methods are generally usable as well. The response signal normally represents a reaction of the fuel mixture to the irradiation of the incoupled signal. For example, this may generally involve transmitted, reflected, remitted or emitted signals or a combination of multiple types of these signals. As an alternative or in addition, inferences can also be drawn from the absorption, i.e., an absence of signal components. The parameter may basically be any quantity that is formed from the incoupled microwave signals and the response signals.

In this context, for instance, it is also possible to form linear combinations of amplitudes and/or phases of the incoupled signals and corresponding variables of the response signals. For example, a difference may be formed between an amplitude of the incoupled microwave radiation and an amplitude of the response microwave radiation, and a difference may be formed from the phase of the incoupled microwave radiation and the phase of the outcoupled microwave radiation. The differences may then constitute the parameter and/or part of this parameter. Depending on the type of comparison of the incoupled signals and the response signals, the parameter, for example, may include at least one of the following parameters: a permittivity, especially a complex permittivity; a dielectric constant, especially a complex dielectric constant; an absorption, in particular a complex absorption; a transmission, especially a complex transmission. Complex variables denote variables which have an amplitude and a phase.

The permittivity, which is frequently also denoted by the letter $\in$, describes the permeability of materials for electric fields. It is a material property of dielectrics materials or of conductive materials featuring only slight electrical conductivity, which manifests itself when electrical fields are applied to these materials. It represents the proportionality constant between electrical flux density D and the electrical field. The dielectric constant, frequently also denoted as $\in_r$ or also as relative permittivity, is the ratio of permittivity $\in$ and the electrical field constant $\in_0$ (permittivity of the vacuum).

In the method provided, microwave signals are coupled in across a frequency range. This means that microwave signals featuring at least two microwave frequencies are coupled in. These two microwave frequencies are able to be coupled in either successively and/or simultaneously. The microwave frequencies may cover a frequency range of at least 100 MHz. The at least two microwave frequencies may cover this frequency range continuously or also in regular or irregular steps. Especially, the incoupled microwave signals may include ultra wide band microwave radiation. Ultra-wide band microwave radiation (UWB) is microwave radiation within the meaning of the above definition, which utilizes an extremely large frequency range, having a bandwidth of at least 500 MHz. As illustrated above, in the method provided the composition of the fuel mixture is inferred from the characteristic of the parameter across the microwave frequency. For example, this characteristic may be determined in a single step, e.g., by determining the parameter across the frequency range simultaneously and/or successively, or an iterative or stepwise determination of the parameters across the frequency range may be performed.

Any analytical, semi-empirical or empirical method may be used to analyze the measured characteristic of the parameter, and thus to determine the composition of the fuel mixture. As a rule, the determination of the composition of the fuel mixture may mean, for instance, determining a concentration of an individual component or of multiple components of this fuel mixture, and/or a mixture ratio. Accordingly, the determination of the composition of the fuel mixture may be performed completely, in the sense of a full analysis, or merely partially, e.g., by determining only the concentration and/or the mixture ratio of an individual component and/or of multiple components. Reference characteristics of the parameters are able to be determined in analytical, empirical or semi-empirical manner, for example.

For instance, the fuel mixture may include at least two, which may be three, four or more components, the individual reference characteristics of the parameter for these components across the frequency of the incoupled microwave signals being known at least partially. For instance, using the afore-described method, these reference characteristics are able to be determined by examining the individual components as pure substances or as essentially pure substances, and parameter characteristics may be recorded in the process. These parameter characteristics of the individual components may then be stored as reference characteristics for the particular component, e.g., in a memory. In the actual measurement of the composition of the fuel mixture, it is then possible to infer the composition of the fuel mixture from the measured characteristic of the actual parameter, by means of the known reference characteristics. This inference of the composition may be obtained, for example, by an individual comparison of the measured characteristic and the reference characteristics and/or an interpolation or extrapolation thereof. Other methods are conceivable as well.

For example, a linear combination of the reference characteristics is possible, in order to thereby adapt the linear combination of the reference characteristics to the measured characteristic. Using the coefficients of the linear combination determined in this adaptation to the measured characteristic, which, for instance, may be determined using known adaptation methods, it will then be possible to infer the proportions of the individual components.

Other options are conceivable as well, however, such as storing a multitude of combinations and corresponding reference characteristics for different fuel mixture compositions in a memory and appropriately selecting reference characteristics having the greatest-possible match from among the measured characteristic of the parameter. This, too, makes it possible to infer the composition of the fuel mixture. In addition, the temperature is able to be measured in close proximity to the fuel volume in order to compensate the temperature-dependency of the measured variables.

In contrast to known devices and methods, the afore-described device and the afore-described method offer numerous advantages. For example, a measuring sensor, through which the fuel mixture is flowing and which is made up of multiple individual components, is realizable, and an uncomplicated and cost-effective manufacture is possible, especially utilizing the afore-described cartridge. Furthermore, a measuring sensor having a reduced volume, without dead volume, is able to be realized. The measuring sensor may have an electromagnetically neutral design, without microwave radiation being applied to the environment of the measuring sensor. The measuring sensor is able to be developed in a cost-effective manner and provided with hydraulic ports that conform to the SAE standard, for example.

Exemplary embodiments of the present invention are shown in the drawing and discussed in greater detail in the following description.

BRIEF DESCRIPTION OF THE DRAWINGS

FIG. 1 shows a cross-section through a device according to the present invention for determining a composition of a fuel mixture, a sectional plane extending parallel to a flow direction.

FIG. 2 shows a perspective view of the device according to FIG. 1.

DETAILED DESCRIPTION

Figure 3:
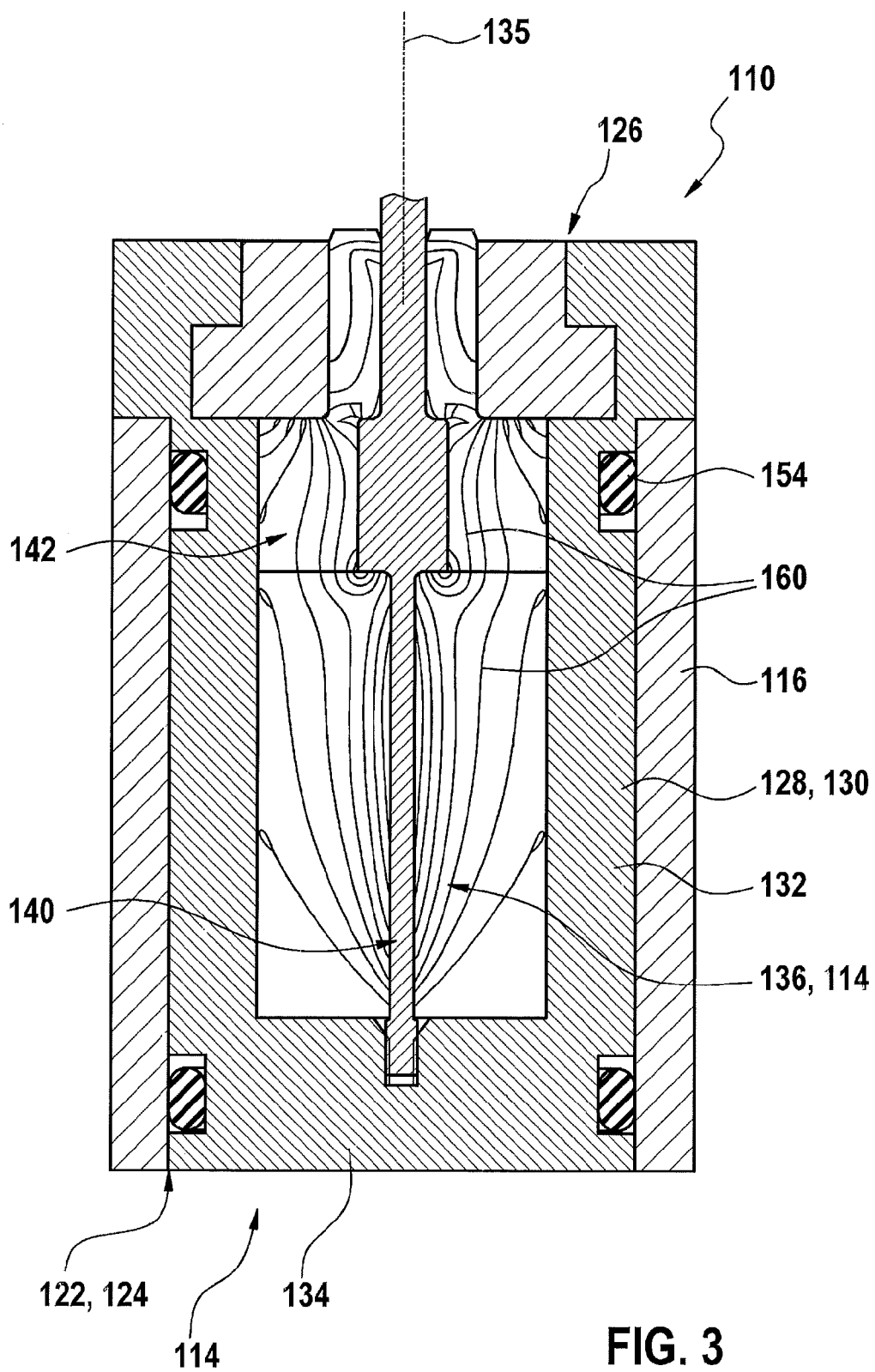
FIG. 3 shows a cross-section through a measuring region of the device according to FIG. 1, a sectional plane extending perpendicularly to the sectional plane according to FIG. 1.

FIGS. 1 through 3 show an exemplary embodiment of a device 110 for determining a composition of a fuel mixture according to the present invention. In particular, it may be used to determine an ethanol component in a fuel. Device 110 is shown in FIG. 1 in a sectional view, featuring a sectional plane parallel to a flow direction 112 of the fuel mixture; in FIG. 2 it is shown in a perspective view; and in FIG. 3 it is shown as a schematic cross-section through device 110, through a measuring region 114, featuring a sectional plane perpendicular to the sectional plane in FIG. 1, the schematic illustration according to FIG. 3 being meant to symbolically illustrate a field line characteristic.

As can be gathered from FIG. 1, device 110 includes a housing 116. Housing 116 includes a flow pipe section 118 provided with hydraulic ports 120, for instance to connect a fuel line. Hydraulic ports 120 may be standardized ports, for example. Furthermore, in a measuring region 114, which in this exemplary embodiment is symmetrically surrounded by hydraulic ports 120 by way of example, housing 116 includes a receptacle 122 provided with a cylindrical receiving bore 124, for instance. Inserted in this receiving bore 124, essentially perpendicularly to flow direction 112, is a plug-in cartridge 126, which constitutes the actual measuring device in the exemplary embodiment at hand. This plug-in cartridge 126 includes a housing element 128 implemented in the form of a metallic cup, through which the flow is able to travel. This cup has a cylindrical cup wall 132 and a cup bottom 134. An axis 135 of cup 130 or plug-in cartridge 126 extending perpendicularly to cup bottom 134 and parallel to cup wall 132, essentially is situated perpendicularly to flow direction 112. Cup wall 132 encloses a measuring volume 136 of measuring region 114. Cup wall 132 is provided with a multitude of bores 138; the bores run at least counter to flow direction 112, facing away from it, and are developed as bore matrix in this exemplary embodiment. Fuel mixture, in FIG. 1 on the left side, is able to enter measuring volume 136 of measuring region 114 through these bores 138 functioning as flow bores, and exit from there again, on the right side in FIG. 1, or vice versa. Plug-in cartridge 126 may be provided with an additional blind hole, for instance on the upper side, which may be used to accommodate a temperature sensor.

In the exemplary embodiment illustrated, housing element 128 or cup 130 concentrically encloses a pin-shaped internal conductor 140. Thus, the fuel mixture flows in measuring volume 136 is flowing around it. Internal conductor 140 is connected to metallic cup bottom 134 at its lower end in that internal conductor 140 is inserted into this cup bottom 134. Above measuring volume 136, internal conductor 140 is embedded in a dielectric 142, such as plastic, by which internal conductor 140 is electrically separated from a plug housing 144. Plug housing 144 is part of a connection device 146, which is developed in the form of a coaxial plug 148 in this case. Apart from plug housing 144, it includes a contact 150 of internal conductor 140. Coaxial plug 150, for example, may be developed as SMA plug.

At its upper end, plug housing 144 is screw-fitted with a cup edge 152 of cup 130. As a result, plug housing 144 and cup 130 may be electrically interconnected. This electrically connects plug housing 144 and cup 130 to each other. Cup 130 itself, for example, may be connected to an external conductor or plug housing of connection device 146, e.g., a coaxial plug. In this way the internal conductor may form a short-circuited coaxial line with the cup. It is possible, as illustrated in FIG. 1, that at least one sealing element 154 is additionally introduced between screw-fitted plug housing 144 and cup 130, the sealing element being implemented in the form of one or multiple O-ring(s), for instance of a fuel-resistant material. One or multiple sealing elements 154 may furthermore also be provided between plug-in cartridge 126 and the wall of receptacle 122 of housing 116, for instance in corresponding annular grooves of cup 130, as sketched in FIG. 1. On the end face of plug-in cartridge 126 situated opposite connection device 146, it may be secured by a locking device 165, such as another screw-fit connection, for example, so that plug-in cartridge 126 is securely anchored in receptacle 122.

Moreover, in the region of plug-in cartridge 126, the flow cross-section widens from an originally small flow cross-section $A_0$ in the region of hydraulic ports 120, to a flow cross-section $A_1$ in the region of measuring volume 136. In the exemplary embodiment illustrated, this widening is continuous and implemented by bushings 158, which may be part of plug-in cartridge 126 and produced from a plastic material, for instance.

Device 110 shown in FIGS. 1 and 2, has a design that is relatively easy to produce, yet effective. The innermost component of device 110, in this case implemented as measuring sensor, is cylindrical cup 130, which may be produced from a corrosion-proof and fuel-compatible material. Situated therein according to the coaxial principle is internal conductor 140, so that plug-in cartridge 126 is basically a coaxial measuring sensor. Internal conductor 140 is conductively connected to cup bottom 134, and the cup itself allows the flow to pass through because of the matrix of bores 138. Overall, the flow-through cross-sections of bores 138 may be dimensioned in such a way that flow-through cross-section $A_0$ is maintained by the total number of bores 138 on one side of cup 130. To broaden the flow, the cross-section of fuel-resistant port $A_0$, which may conform to the SAE standard, becomes continuously wider until reaching the bore matrix cross-section, with the aid of inserted bushing 158. The bore diameter of individual bores 138 may be small in relation to the minimal wavelength arising in the fuel mixture. This avoids an undesired radiation into the environment. The measuring principle of device 110 according to FIGS. 1 and 2 will be explained by way of example based on the sectional view shown in FIG. 3. As explained earlier, this view illustrates a sectional view perpendicular to the sectional plane in FIG. 1, through axis 135. It should be pointed out that this is merely a schematic illustration, which will be used to explain the extension of electrical field lines 160 for a single frequency.

Via connection device 146, such as via a coaxial standardized plug connector (e.g., SMA-RP), device 110 is able to be connected to a high frequency (HF) sensor circuit. In this way microwave signals or generally high-frequency signals of different frequencies may be applied to device 110, and response signals may be recorded using the same connection device 146. As a result, connection device 146 may be used simultaneously for an incoupling of microwave signals and for an outcoupling of response signals. Using the incoupled signal and response signal makes it possible to determine one or multiple parameter(s) as well as the characteristic of these parameters across the frequency of the incoupled radiation. One essential parameter is the permittivity, as described above. For example, using a difference (amplitude and phase) between emitted or incoupled and received signal or response signal, it is possible to infer the permittivity of the fuel mixture located inside the measuring volume. The characteristic of the permittivity and/or of one or multiple alternative parameter(s) across the frequency is used to identify and quantify individual components of the fuel mixture. As described above, a comparison with reference curves may be carried out for this purpose, for instance by adapting linear coefficients, e.g., while minimizing error squares, or using similar adaptation methods.

Depending on the loss characteristics of the fuel mixture (described, for instance, by the imaginary component of the permittivity of the fuel mixture), fuel-filled measuring volume 136 in the form of filled coaxial line section has a damping and, depending on the real component of the permittivity, a delaying effect on emitted and reflected waves. The reflected wave experiences a defined phase shift of 180°, for example, at the end of the short-circuited coaxial line in the region of cup bottom 134.

The parameter is determined at different frequencies across the largest possible frequency range. For instance, this may be accomplished using an ultra wide band sensor (UWB). When using a UWB, the permittivity is determined not only at individual frequency lines, but also their characteristic across the entire measured frequency range, e.g., a frequency range of 1.5 GHz to 8.5 GHz. This increases the information content of the measurement considerably. Over all, this makes it possible to provide a measuring device which is simple to produce, cost-effective and easy to manage and which seals in reliable manner; this measuring device, for instance, is able to be used in motor vehicles, especially Otto engines, but also in Diesel engines.

What is claimed is:

1. A device for determining a composition of a fuel mixture, comprising:
    at least one housing having at least one electrically conductive housing element through which the fuel mixture is able to flow, wherein at least one internal conductor is introduced into the housing element, the at least one internal conductor being at least partially surrounded by the housing element; and
    at least one connection device for coupling microwave signals,
    wherein the housing element has at least one cup which at least partially surrounds the internal conductor,
    wherein the cup has a plurality of bores, the bores having a diameter which is smaller than the smallest wavelength of the incoupled microwaves.

2. The device of claim 1, wherein the housing element encloses the internal conductor in a coaxial manner.

3. The device of claim 1, wherein the connection device has at least one coaxial plug, and wherein the coaxial plug has at least one contact to apply microwave signals to the internal conductor.

4. The device of claim 1, wherein the bores have a diameter which is smaller than 1 mm.

5. The device of claim 1, wherein the bores have a diameter which is smaller than 2 mm.

6. A device for determining a composition of a fuel mixture, comprising:
    at least one housing having at least one electrically conductive housing element through which the fuel mixture is able to flow, wherein at least one internal conductor is introduced into the housing element, the at least one internal conductor being at least partially surrounded by the housing element;
    at least one connection device for coupling microwave signals; and
    at least one flow pipe section through which the fuel mixture is able to flow in a flow direction, wherein the internal conductor and the housing element are introduced into the flow pipe section transversely to the flow direction.

7. The device of claim 6, wherein the housing element has at least one cup which at least partially surrounds the internal conductor.

8. The device of claim 7, wherein the cup is connected to the internal conductor in an electrically conductive manner.

9. A device for determining a composition of a fuel mixture, comprising:
    at least one housing having at least one electrically conductive housing element through which the fuel mixture is able to flow, wherein at least one internal conductor is introduced into the housing element, the at least one internal conductor being at least partially surrounded by the housing element;
    at least one connection device for coupling microwave signals; and
    a plug-in cartridge, which accommodates the internal conductor and the housing element, wherein the plug-in cartridge is plugged into a receptacle of the flow pipe section in a measuring region transversely to the flow direction.

10. The device of claim 9, wherein the plug-in cartridge is sealed from the flow pipe section by at least one sealing element.

11. A device for determining a composition of a fuel mixture, comprising:
    at least one housing having at least one electrically conductive housing element through which the fuel mixture is able to flow, wherein at least one internal conductor is introduced into the housing element, the at least one internal conductor being at least partially surrounded by the housing element; and
    at least one connection device for coupling microwave signals; and
    a flow pipe section through which the fuel mixture is able to flow, wherein the housing element and the internal conductor are accommodated in a measuring region, and wherein a flow pipe cross-section in the measuring region is broadened compared to a flow pipe cross-section outside the measuring region.

12. A device for determining a composition of a fuel mixture, comprising:
    at least one housing having at least one electrically conductive housing element through which the fuel mixture is able to flow, wherein at least one internal conductor is introduced into the housing element, the at least one internal conductor being at least partially surrounded by the housing element; and
    at least one connection device for coupling microwave signals,
    wherein the device is for determining at least one of an ethanol component and a water component in the fuel mixture.

13. A device for determining a composition of a fuel mixture, comprising:
    at least one housing having at least one electrically conductive housing element through which the fuel mixture is able to flow, wherein at least one internal conductor is introduced into the housing element, the at least one internal conductor being at least partially surrounded by the housing element;
    at least one connection device for coupling microwave signals; and
    at least one flow pipe section through which the fuel mixture is able to flow in a flow direction, wherein the internal conductor and the housing element are introduced into the flow pipe section substantially perpendicularly to the flow direction.

14. A device for determining a composition of a fuel mixture, comprising:
    at least one housing having at least one electrically conductive housing element through which the fuel mixture is able to flow, wherein at least one internal conductor is introduced into the housing element, the at least one internal conductor being at least partially surrounded by the housing element;
    at least one connection device for coupling microwave signals;
    at least one flow pipe section through which the fuel mixture is able to flow in a flow direction, wherein the housing includes the flow pipe section; and
    a plug-in cartridge, which accommodates the internal conductor and the housing element, wherein the plug-in cartridge is plugged into a receptacle of the flow pipe section in a measuring region transversely to the flow direction, wherein the housing element has at least one cup which at least partially surrounds the internal conductor, wherein the cup is connected to the internal conductor in an electrically conductive manner, wherein the internal conductor and the housing element are introduced into the flow pipe section transversely to the flow direction.

15. A method for determining a composition of a fuel mixture, the method comprising:

coupling, using a device, microwave signals are coupled into the fuel mixture across a frequency range, wherein the device includes at least one housing having at least one electrically conductive housing element through which the fuel mixture is able to flow, wherein at least one internal conductor is introduced into the housing element, the at least one internal conductor being at least partially surrounded by the housing element, and wherein the device includes at least one connection device for coupling microwave signals;

receiving response signals using the device;

determining at least one parameter from a comparison of the incoupled microwave signals and the response signals, as a function of the microwave frequency of the incoupled microwave signals; and inferring a composition of the fuel mixture from a characteristic of the parameter across the microwave frequency.

* * * * *